United States Patent [19]

Krämer

[11] 4,293,715
[45] Oct. 6, 1981

[54] PREPARATION OF ω-AZOLYL-ACETOPHENONE OXIDE ETHERS EMPLOYING ω-HALOGENO-ACETOPHENONE OXIDE ETHERS

[75] Inventor: Wolfgang Krämer, Wuppertal, Fed. Rep. of Germany

[73] Assignee: Bayer Aktiengesellschaft, Leverkusen, Fed. Rep. of Germany

[21] Appl. No.: 120,168

[22] Filed: Feb. 11, 1980

[30] Foreign Application Priority Data

Mar. 1, 1979 [DE] Fed. Rep. of Germany ....... 2907972

[51] Int. Cl.³ ................. C07C 131/00; C07D 233/61; C07D 249/08
[52] U.S. Cl. ............................... 564/256; 260/465 E; 548/262; 548/341
[58] Field of Search .................... 260/566 AE, 465 E; 564/256

[56] References Cited

U.S. PATENT DOCUMENTS 3,732,306  8/1973  Gutman et al. ............. 260/566 AE
3,914,300 10/1975  Haddock et al. ........... 260/566 AE
4,052,194 10/1977  Wilcox ....................... 260/566 AE

FOREIGN PATENT DOCUMENTS 1096037 12/1967 United Kingdom ................ 564/256

OTHER PUBLICATIONS

Huisgen et al., Chem. Abstracts, vol. 54, Abstract 3294g (1960).

Primary Examiner—Alton D. Rollins
Attorney, Agent, or Firm—Sprung, Felfe, Horn, Lynch & Kramer

[57] ABSTRACT

In the preparation of an ω-azolyl-acetophenone oxime ether of the formula

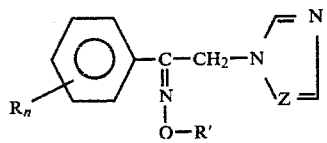

in which
R is halogen, alkyl, alkoxy, alkylthio, alkylsulphonyl, halogenoalkyl, nitro, cyano, optionally substituted phenyl or optionally substituted phenoxy,
R' is alkyl, alkenyl, alkynyl, optionally substituted cycloalkylalkyl, optionally substituted aralkyl or optionally substituted aralkenyl,
n is 1, 2 or 3,
Hal is halogen, and
Z is CH or N, wherein the ω-halogen of an ω-halogeno-acetophenone of the formula

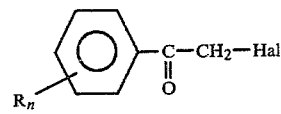

is replaced by an azole of the formula

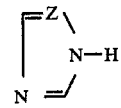

and the keto oxygen is replaced by

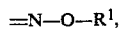

the improvement which comprises first reacting the ω-halogeno-acetophenone with a hydroxylamine ether of the formula

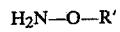

to produce an ω-halogeno-acetophenone oxime ether of the formula

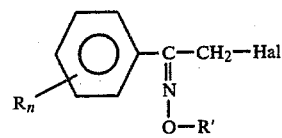

and reacting the acetophenone oxime ether with the azole, thereby to obtain the desired product in enhanced yield. The intermediate acetophenone oxime ethers are new.

6 Claims, No Drawings

PREPARATION OF ω-AZOLYL-ACETOPHENONE OXIDE ETHERS EMPLOYING ω-HALOGENO-ACETOPHENONE OXIDE ETHERS

The present invention relates to certain new ω-halogeno-acetophenone oxime ethers, to a process for their preparation and to their use as intermediate products for the preparation of ω-azolyl-acetophenone oxime ethers which are largely known and have a fungicidal and bactericidal action.

It has already been disclosed that fungicidally active ω-azolyl-acetophenone oxime ethers are obtained when corresponding ω-azolyl-acetophenones are converted into the ω-azolyl-acetophenone oximes with hydroxylamine and the oximes are reacted with a halogen derivative (see DE-OS (German Published Specification) No. 2,657,578 and DE-OS (German Published Specification) No. 2,723,942). However, this synthesis route has some disadvantages.

The present invention now provides, as new compounds, the ω-halogeno-acetophenone oxime ethers of the general formula

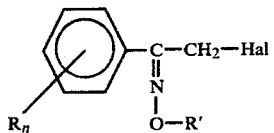
(I)

in which
R represents halogen, alkyl, alkoxy, alkylthio, alkylsulphonyl, halogenoalkyl, nitro, cyano, optionally substituted phenyl or optionally substituted phenoxy,
R' represents alkyl, alkenyl, alkynyl, optionally substituted cycloalkylalkyl, optionally substituted aralkyl or optionally substituted aralkenyl,
n represents the integer 1, 2 or 3 and
Hal represents halogen.

The compounds of the formula (I) can exist in the syn-form or anti-form; they are predominantly obtained as mixtures of the two forms.

The invention also provides a process for the preparation of an ω-halogeno-acetophenone oxime ether of the general formula (I) in which an ω-halogeno-acetophenone of the general formula

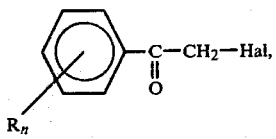
(II)

in which Hal, R and n have the meanings indicated above, is reacted with a substituted hydroxylamine of the general formula $$H_2N-O-R' \quad (III),$$

in which R' has the meaning indicated above, in the presence of a diluent.

The compounds of the formula (I) are interesting intermediate products for the preparation of ω-azolyl-acetophenone oxime ethers, which are known (see DE-OS (German Published Specification) No. 2,657,578 and DE-OS (German Published Specification) No. 2,723,942), of the general formula

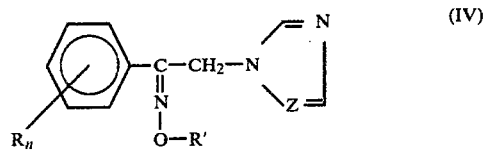
(IV)

in which R, R' and n have the meanings indicated above and Z represents a CH group or a nitrogen atom.

The known end products of the formula (IV) obtainable from the new intermediate products of the formula (I) are active compounds with a fungicidal action and also a bactericidal action and can be used, for example, as plant protection agents. As will also be shown, the end products (IV) can be built up in a simple manner from the new intermediate products (I) and the new synthesis route has a number of advantages compared with the route already known.

The formula (I) provides a general definition of the substances according to the invention. Preferably, in this formula, R represents fluorine, chlorine, bromine, nitro, cyano, alkyl or alkylsulphonyl with in either case 1 to 4 carbon atoms, alkoxy or alkylthio with in either case 1 to 2 carbon atoms, halogenoalkyl with up to 4 carbon atoms and up to 5 halogen atoms (especially with up to 2 carbon atoms and up to 3 identical or different halogen atoms, preferred halogen atoms being fluorine and chlorine and trifluoromethyl being mentioned as a specific example of halogenoalkyl), or phenyl or phenoxy, either of which optionally carries one or more substituents selected independently from halogen (especially fluorine, chlorine or bromine), cyano, nitro and halogenoalkyl with up to 2 carbon atoms and up to 3 identical or different halogen atoms (preferred halogen atoms being fluorine and chlorine and trifluoromethyl being mentioned as a specific example of halogenoalkyl), R' represents alkyl, alkenyl or alkynyl with in each case up to 4 carbon atoms, cycloalkylalkyl with 5 to 7 carbon atoms in the cycloalkyl part and 1 to 2 carbon atoms in the alkyl part, it being possible for the cycloalkyl part to be optionally substituted by alkyl with 1 to 4 carbon atoms, or benzyl or styryl, either of which optionally carries one or more substitutents, selected independently from halogen (especially fluorine, chlorine or bromine), cyano, nitro, amino, alkyl with 1 to 4 carbon atoms, phenyl, phenoxy and halogenoalkyl with up to 2 carbon atoms and up to 3 identical or different halogen atoms (preferred halogen atoms being fluorine and chlorine and trifluoromethyl being mentioned as a specific example of halogenoalkyl), n represents the number 1 or 2 and
Hal represents chlorine or bromine.

The particularly preferred ω-halogeno-acetophenone oxime ethers of the formula (I) are those in which R represents chlorine, bromine, phenyl, chlorophenyl, bromophenyl, nitrophenyl, phenoxy, chlorophenoxy, bromophenoxy or nitrophenoxy; n represents the number 1 or 2; and R' represents methyl, ethyl, n-propyl, isopropyl, n-butyl, isobutyl, sec.-butyl, tert.-butyl, allyl, 2-methallyl, propargyl, cyclohexylmethyl, methylcyclohexylmethyl, benzyl (which can optionally be monosubstituted or disubstituted, the substituent(s) being selected from chlorine, bromine, nitro, methyl, ethyl, phenyl and phenoxy) or styryl which is optionally monosubstituted or disubstituted by chlorine.

The compounds in the following table may be mentioned specifically:

(Ia)

| $R_n$ | R' |
|---|---|
| 2,4-Cl$_2$ | —CH$_2$—C$_6$H$_4$—Cl |
| 2,4-Cl$_2$ | —CH$_2$—C$_6$H$_3$(Cl)(Cl) |
| 2,4-Cl$_2$ | —CH$_2$—C$_6$H$_3$(Cl)(Cl) |
| 2,4-Cl$_2$ | —CH$_2$—C$_6$H$_4$—Cl |
| 2,4-Cl$_2$ | —CH$_2$—C$_6$H$_4$—F |
| 2,4-Cl$_2$ | —CH$_2$—C$_6$H$_4$—NO$_2$ |
| 2,4-Cl$_2$ | —CH$_2$—C$_6$H$_5$ |
| 2,4-Cl$_2$ | CH$_3$ |
| 2,4-Cl$_2$ | C$_2$H$_5$ |
| 2,4-Cl$_2$ | C$_3$H$_7$ |
| 2,4-Cl$_2$ | C$_4$H$_9$ |
| 2,4-Cl$_2$ | —CH$_2$—CH=CH$_2$ |
| 2,4-Cl$_2$ | —CH$_2$—C≡CH |
| 2,5-Cl$_2$ | —CH$_2$—C$_6$H$_4$—Cl |
| 2,5-Cl$_2$ | —CH$_2$—C$_6$H$_3$(Cl)(Cl) |
| 2,5-Cl$_2$ | —CH$_2$—C$_6$H$_3$(Cl)(Cl) |
| 2,5-Cl$_2$ | —CH$_2$—C$_6$H$_4$—Cl |
| 2,5-Cl$_2$ | —CH$_2$—C$_6$H$_4$—F |
| 2,5-Cl$_2$ | —CH$_2$—C$_6$H$_4$—NO$_2$ |
| 2,5-Cl$_2$ | —CH$_2$—C$_6$H$_5$ |
| 2,5-Cl$_2$ | CH$_3$ |
| 2,5-Cl$_2$ | C$_2$H$_5$ |
| 2,5-Cl$_2$ | C$_3$H$_7$ |
| 2,5-Cl$_2$ | C$_4$H$_9$ |
| 2,5-Cl$_2$ | —CH$_2$—CH=CH$_2$ |
| 2,5-Cl$_2$ | —CH$_2$—C≡CH |
| 3,4-Cl$_2$ | —CH$_2$—C$_6$H$_4$—Cl |
| 3,4-Cl$_2$ | —CH$_2$—C$_6$H$_4$—Cl |
| 3,4-Cl$_2$ | —CH$_2$—C$_6$H$_3$(Cl)(Cl) |
| 3,4-Cl$_2$ | —CH$_2$—C$_6$H$_3$(Cl)(Cl) |
| 3,4-Cl$_2$ | —CH$_2$—C$_6$H$_4$—Cl |
| 3,4-Cl$_2$ | —CH$_2$—C$_6$H$_4$—F |
| 3,4-Cl$_2$ | —CH$_2$—C$_6$H$_4$—NO$_2$ |
| 3,4-Cl$_2$ | —CH$_2$—C$_6$H$_5$ |
| 3,4-Cl$_2$ | CH$_3$ |
| 3,4-Cl$_2$ | C$_2$H$_5$ |
| 3,4-Cl$_2$ | C$_3$H$_7$ |
| 3,4-Cl$_2$ | C$_4$H$_9$ |
| 3,4-Cl$_2$ | —CH$_2$—CH=CH$_2$ |
| 3,4-Cl$_2$ | —CH$_2$—C≡CH$_2$ |
| 4-Cl | —CH$_2$—C$_6$H$_4$—Cl |
| 4-Cl | —CH$_2$—C$_6$H$_3$(Cl)(Cl) |
| 4-Cl | —CH$_2$—C$_6$H$_3$(Cl)(Cl) |
| 4-Cl | —CH$_2$—C$_6$H$_4$—Cl |
| 4-Cl | —CH$_2$—C$_6$H$_4$—F |
| 4-Cl | —CH$_2$—C$_6$H$_4$—NO$_2$ |
| 4-Cl | —CH$_2$—C$_6$H$_5$ |
| 4-Cl | CH$_3$ |
| 4-Cl | C$_2$H$_5$ |
| 4-Cl | C$_3$H$_7$ |
| 4-Cl | C$_4$H$_9$ |
| 4-Cl | —CH$_2$—CH=CH$_2$ |
| 4-Cl | —CH$_2$—C≡CH |
| 4-Br | —CH$_2$—C$_6$H$_4$—Cl |
| 4-Br | —CH$_2$—C$_6$H$_3$(Cl)(Cl) |

4,293,715

-continued (Ia)

structure: Ar(Rn)-C(=N-O-R')-CH₂-Cl(Br) where Ar is phenyl

| Rn | R' |
|---|---|
| 4-Br | —CH₂—(2,3-dichlorophenyl) |
| 4-Br | —CH₂—(2,4-dichlorophenyl) |
| 4-Br | —CH₂—(4-fluorophenyl) |
| 4-Br | —CH₂—(4-nitrophenyl) |
| 4-Br | —CH₂—(phenyl) |
| 4-Br | CH₃ |
| 4-Br | C₂H₅ |
| 4-Br | C₃H₇ |
| 4-Br | C₄H₉ |
| 4-Br | —CH₂—CH=CH₂ |
| 4-Br | —CH₂—C≡CH₂ |
| 4-phenyl | —CH₂—(4-chlorophenyl) |
| 4-phenyl | —CH₂—(2,4-dichlorophenyl) |
| 4-phenyl | —CH₂—(2,3-dichlorophenyl) |
| 4-phenyl | —CH₂—(2,4-dichlorophenyl) |
| 4-phenyl | —CH₂—(4-fluorophenyl) |
| 4-phenyl | —CH₂—(4-nitrophenyl) |
| 4-phenyl | —CH₂—(phenyl) |
| 4-phenyl | CH₃ |
| 4-phenyl | C₂H₅ |
| 4-phenyl | C₃H₇ |
| 4-phenyl | C₄H₉ |
| 4-phenyl | —CH₂—CH=CH₂ |
| 4-phenyl | —CH₂—C≡CH |
| 4-Cl-phenyl | —CH₂—(4-chlorophenyl) |
| 4-Cl-phenyl | —CH₂—(2,4-dichlorophenyl) |
| 4-Cl-phenyl | —CH₂—(2,3-dichlorophenyl) |
| 4-Cl-phenyl | —CH₂—(2,4-dichlorophenyl) |
| 4-Cl-phenyl | —CH₂—(4-fluorophenyl) |
| 4-Cl-phenyl | —CH₂—(4-nitrophenyl) |
| 4-Cl-phenyl | —CH₂—(phenyl) |
| 4-Cl-phenyl | CH₃ |
| 4-Cl-phenyl | C₂H₅ |
| 4-Cl-phenyl | C₃H₇ |
| 4-Cl-phenyl | C₄H₉ |
| 4-Cl-phenyl | —CH₂—CH=CH₂ |
| 4-Cl-phenyl | —CH₂—C≡CH₂ |
| 4-(phenyl-O—) | —CH₂—(4-chlorophenyl) |
| 4-(phenyl-O—) | —CH₂—(2,4-dichlorophenyl) |
| 4-(phenyl-O—) | —CH₂—(2,3-dichlorophenyl) |
| 4-(phenyl-O—) | —CH₂—(2,4-dichlorophenyl) |
| 4-(phenyl-O—) | —CH₂—(4-fluorophenyl) |
| 4-(phenyl-O—) | —CH₂—(4-nitrophenyl) |
| 4-(phenyl-O—) | —CH₂—(phenyl) |
| 4-(phenyl-O—) | CH₃ |
| 4-(phenyl-O—) | C₂H₅ |
| 4-(phenyl-O—) | |

-continued

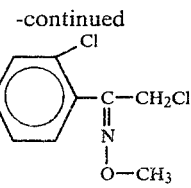

The formula (II) provides a general definition of the ω-halogeno-acetophenones to be used as starting materials for the preparation of the compounds of the formula (I). In this formula, Hal, R and n preferably have those meanings which have already been mentioned as preferred in connection with the description of the compounds of the formula (I).

The ω-halogeno-acetophenones are known (see Bulletin de la Societe Chimique de France 1955, pages 1363-1393). They can be prepared in a generally known manner, for example by reacting corresponding benzenes with chloroacetyl or bromoacetyl chloride in a Friedel-Crafts reaction or by halogenating corresponding acetophenones in the customary manner, preferred halogenating agents being sulphuryl chloride or bromine.

Examples of ω-halogeno-acetophenones which may be mentioned are: ω-chloro(bromo)-4-chloroacetophenone, ω-chloro(bromo)-2,4-dichloroacetophenone, ω-chloro(bromo)-3,4-dichloroacetophenone, ω-chloro(bromo)-4-bromoacetophenone, ω-chloro(bromo)-4-nitroacetophenone, ω-chloro(bromo)-4-cyanoacetophenone, ω-chloro(bromo)-2-methylacetophenone, ω-chloro(bromo)-2-methoxyacetophenone, ω-chloro(bromo)-2-ethyl-4-chloroacetophenone, ω-chloro(bromo)-2-ethylthioacetophenone, ω-chloro(bromo)-4-methylsulphonylacetophenone, ω-chloro(bromo)-2,4,5-trichloroacetophenone, ω-chloro(bromo)-4-phenylacetophenone, ω-chloro(bromo)-4-4'-chlorophenylacetophenone, ω-chloro(bromo)-4-4'-bromophenylacetophenone, ω-chloro(bromo)-4-4'-nitrophenylacetophenone, ω-chloro(bromo)-4-phenoxyacetophenone, ω-chloro(bromo)-4-4'-chlorophenoxyacetophenone, ω-chloro(bromo)-4-4'-bromophenoxyacetophenone and ω-chloro(bromo)-4-4'-nitrophenoxyacetophenone.

The formula (III) provides a general definition of the substituted hydroxylamines also to be used as starting materials. In this formula, R' preferably has the meanings which have already been mentioned as preferred in connection with the description of the compounds of the formula (I).

The substituted hydroxylamines of the formula (III) are generally known compounds of organic chemistry. Examples which may be mentioned are: O-methyl-hydroxylamine, O-ethyl-hydroxylamine, O-n-propyl-hydroxylamine, O-isopropyl-hydroxylamine, O-n-butyl-hydroxylamine, O-tert.-butyl-hydroxylamine, O-allyl-hydroxylamine, O-2-methallyl-hydroxylamine, O-propargyl-hydroxylamine, O-4-chlorobenzyl-hydroxylamine, O-2-chlorobenzyl-hydroxylamine, O-2,4-dichlorobenzyl-hydroxylamine, O-3,4-dichlorobenzyl-hydroxylamine, O-2,6-dichlorobenzyl-hydroxylamine, O-2,5-dichlorobenzyl-hydroxylamine, O-4-bromobenzylhydroxylamine, O-4-fluorobenzyl-hydroxylamine, O-4-nitrobenzyl-hydroxylamine, O-4-methylbenzyl-hydroxylamine, O-4-phenoxybenzyl-hydroxylamine, O-3-phenoxybenzyl-hydroxylamine, O-4-phenylbenzyl-hydroxylamine, O-styryl.hydroxylamine, O-2,4-

(Ia)

| $R_n$ | R' |
|---|---|
| 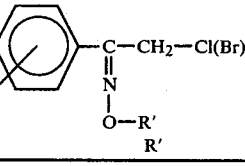 | $C_3H_7$ |
|  | $C_4H_9$ |
|  | $-CH_2-CH=CH_2$ |
|  | $-CH_2-C\equiv CH$ |
|  | $CH_3$ |
|  | $C_2H_5$ |
|  | $C_3H_7$ |
|  | $C_4H_9$ |
|  | $-CH_2-CH=CH_2$ |
|  | $-CH_2-C\equiv CH$ |
|  |  |
| 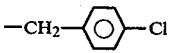 |  |
| 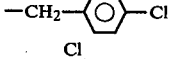 |  |
| 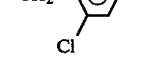 |  |
| 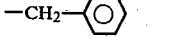 |  |
| 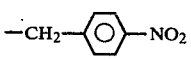 |  |
| 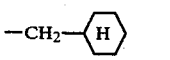 |  |

If, for example, ω-chloro-2,4-dichloroacetophenone and O-methyl-hydroxylamine hydrochloride are used as starting materials, the course of the reaction can be represented by the following equation:

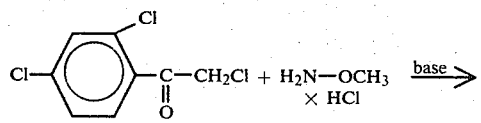

dichlorostyryl-hydroxylamine, O-cyclohexylmethyl-hydroxylamine and O-methylcyclohexylmethyl-hydroxylamine.

Preferred diluents for use in the preparation of the compounds of the formula (I) are alcohols or aqueous alcohols.

The reaction temperatures can be varied within a substantial range. In general, the reaction is carried out at from 20° to 120° C., preferably from 50° to 100° C.

In carrying out the process according to the invention, 1 to 1.2 mols of hydroxylamine of the formula (III) are preferably employed per mol of acetophenone of the formula (II). The compounds of the formula (I) are isolated by customary methods.

According to a preferred embodiment, the hydroxylamines of the formula (III) are employed in the form of their salts, especially as the hydrochlorides, if appropriate in the presence of an acid-binding agent, for example sodium acetate (see also the preparative examples).

As already mentioned, the compounds of the formula (I) can advantageously be used to prepare the known active compounds of the formula (IV).

It is known, according to the state of the art, that a fungicidally active ω-azolyl-acetophenone oxime ether is obtained when, in a first stage, an ω-halogenoacetophenone is reacted with an azole (1,2,4-triazole or imidazole) in the presence of an inert organic solvent and in the presence of an acid-binding agent, at a temperature between 20° and 120° C.; the ω-azolyl-acetophenone formed is reacted, in a second stage, with hydroxylamine in the presence of a solvent, preferably an alcohol, at 50° to 80° C., the hydroxylamine preferably being employed as the hydrochloride in the presence of an acid-binding agent; and the ω-azolyl-acetophenone oxime formed is reacted, in a third stage, with a halogen derivative in the presence of an inert organic solvent and if appropriate in the presence of a strong base, at temperatures between 60° and 100° C., to give the corresponding ether, according to the following equations (see DE-OS (German Published Specification) No. 2,657,578 and DE-OS (German Published Specification) No. 2,723,942):

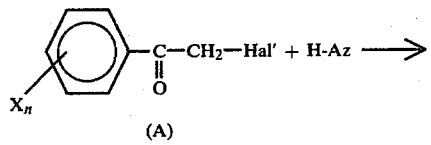

(A)

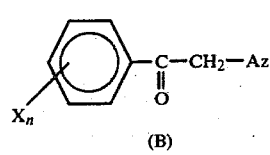

(B)

(B) + H₂N—OH ⟶

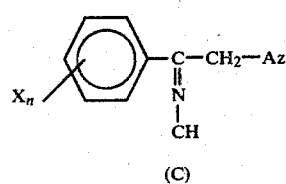

(C)

(C) + Y-Hal' ⟶

-continued

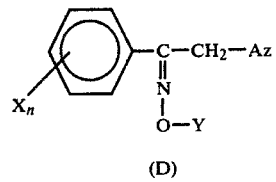

(D)

In these equations:

As denotes 1,2,4-triazolyl or imidazolyl;

X denotes halogen, alkyl, alkoxy, nitro, optionally substituted phenyl or optionally substituted phenoxy;

Hal' denotes halogen;

Y denotes alkyl, alkenyl, alkynyl, cycloalkyl or optionally substituted aralkyl; and n denotes 0, 1, 2 or 3.

This known process has the disadvantage that it does not proceed to a satisfactory total yield of the ω-azolylacetophenone oxime ether of the formula (D).

As has now also been found, an ω-azolyl-acetophenone oxime ether of the general formula

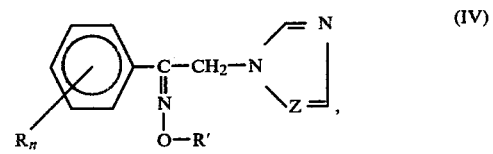

in which R, R', Z and n have the meanings given initially, is obtained in a particularly advantageous manner when an ω-halogeno-acetophenone oxime ether of the general formula

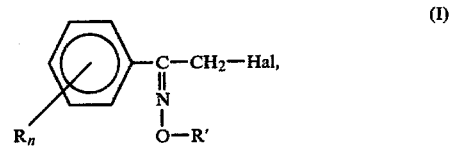

in which Hal, R, R' and n have the meanings given initially, is reacted with an azole of the general formula

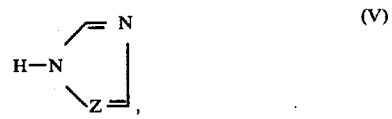

in which Z has the meaning indicated initially, in the presence of an acid-binding agent and in the presence of a diluent.

It is surprising that the desired end products can be obtained in a high yield and purity by the route via the new intermediate products of the formula (I), whereupon this process proves to be more advantageous, compared with the synthesis route known from the state of the art.

If, for example, ω-chloro-2,4-dichloroacetophenone oxime O-methyl ether and 1,2,4-triazole are used as the starting materials, the course of the reaction can be represented by the following equation:

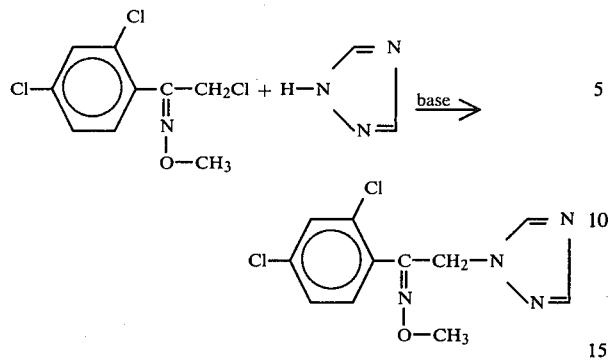

The formula (V) provides a general definition of the azoles to be used as starting materials for the preparation of the end products of the formula (IV). In formula (V), Z represents a CH group or a nitrogen atom.

The azoles of the formula (V) are generally known compounds of organic chemistry.

The following details should also be noted with regard to the preparation of the end products of the formula (IV):

Preferred diluents are inert organic solvents. These include ketones, such as acetone and methyl ethyl ketone; nitriles, such as acetonitrile; alcohols, such as ethanol; ethers, such as tetrahydrofuran or dioxane; aromatic hydrocarbons, such as toluene and benzene; formamides, such as dimethylformamide; and halogenated hydrocarbons, such as methylene chloride, carbon tetrachloride or chloroform.

The reaction is carried out in the presence of an acid-binding agent. It is possible to add any of the inorganic or organic acid-binding agents which can customarily be used, such as alkali metal carbonates, for example sodium carbonate and potassium carbonate, or such as lower tertiary alkylamines, cycloalkylamines or aralkylamines, for example triethylamine, N,N-dimethylcyclohexylamine and N,N-dimethylbenzylamine. An appropriate excess of azole of the formula (V) can also be used.

The reaction temperatures can be varied within a substantial range. In general, the reaction is carried out at from 0° to 150° C., preferably at 60° to 120° C.

For carrying out the reaction, 1 to 2 mols of azole and 1 to 2 mols of acid-binding agent are preferably employed per mol of the compound of the formula (I). The resultant compound of the formula (IV) is isolated by customary methods. Since these compounds are usually obtained in the form of oils, they are preferably isolated as salts, especially as hydrochlorides or nitrates.

According to a particular embodiment, a procedure can also be followed in which the intermediate of the formula (I) according to the invention is first prepared and then reacted further without isolating it and without changing the solvent, and the ω-azolyl-acetophenone oxime ether (end products of the formula (IV) is obtained in one operation by a "one-pot process".

As is known, the ω-azolyl-acetophenone oxime ethers of the formula (IV) are distinguished by a very good fungicidal activity (see DE-OS (German Published Specification) No. 2,657,578 and DE-OS (German Published Specification) No. 2,723,942).

In the preparative examples, the new route for the preparation of the known compounds of the formula (IV) via the new intermediate products of the formula (I) is illustrated and compared with the known processes.

PREPARATIVE EXAMPLES (A) New intermediate products of the formula (I)

EXAMPLE A1

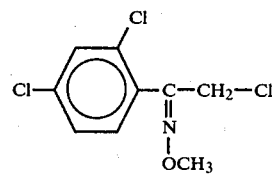

22.3 g (0.1 mol) of ω-chloro-2,4-dichloroacetophenone were heated under reflux with 9.2 g (0.11 mol) of O-methyl-hydroxylamine hydrochloride and 8.2 g (0.1 mol) of sodium acetate in 200 ml of ethanol for 20 hours. Thereafter, the solvent was distilled off in vacuo and the residue was taken up in 100 ml of methylene chloride. The methylene chloride mixture was washed once with 200 ml of water and twice with 100 ml of water each time, dried over sodium sulphate and concentrated by distilling off the solvent in vacuo. 25 g (99.6% of theory) of ω-chloro-2,4-dichloroacetophenone oxime O-methyl ether were obtained as an oil with a refractive index of $n_D^{20} = 1.5652$.

The following compounds of the general formula

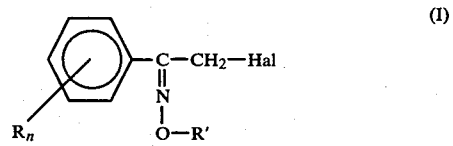

were obtained in a corresponding manner:

| Example No. | $R_n$ | R' | Hal | Physical Constant |
|---|---|---|---|---|
| A 2 | 2,4-Cl$_2$ | —CH$_2$—(3,4-Cl$_2$-C$_6$H$_3$) | Cl | $n_D^{20} = 1.5901$ |
| A 3 | 2,4-Cl$_2$ | —CH$_2$—(4-Cl-C$_6$H$_4$) | Cl | $n_D^{23} = 1.5879$ |

(B) End products of the formula (IV)

EXAMPLE B1

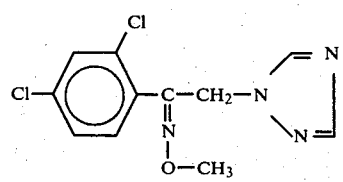

[Preparation according to the invention, with isolation of the intermediate product]:

ω-Chloro-2,4-dichloroacetophenone oxime O-methyl ether was first prepared according to Example A1 (see above). The procedure then was as follows:

12.5 g (0.05 mol) of ω-chloro-2,4-dichloroacetophenone oxime O-methyl ether were dissolved in 10 ml of dimethylformamide and the solution was added dropwise to 4 g (0.055 mol) of 1,2,4-triazole and 7 g (0.05 mol) of potassium carbonate in 50 ml of dimethylformamide. After the dropwise addition, the reaction mixture was stirred at 70° C. for 20 hours and, after cooling, was stirred into 200 ml of water. Thereafter, the mixture was extracted with 200 ml of methylene chloride and the organic phase was washed eight times with 100 ml of water each time, dried over sodium sulphate and concentrated by distilling off the solvent in vacuo. 12 g (84.5% of theory) of ω-(1,2,4-triazol-1-yl)-2,4-dichloroacetophenone oxime O-methyl ether (which corresponded to a total yield of 84.2% of theory) were obtained as an oil which could be converted into the corresponding nitrate of decomposition point 90°–92° C. by treatment with nitric acid in chloroform.

COMPARISON EXAMPLE

[Preparation by the previously known process] 1st stage

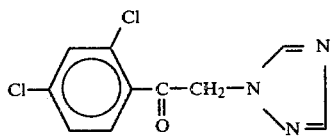

269 g (1 mol) of ω-bromo-2,4-dichloroacetophenone were dissolved in 250 ml of acetonitrile. This solution was added dropwise to a suspension, boiling under reflux, of 69 g (1 mol) of 1,2,4-triazole and 150 g of potassium carbonate in 2,000 ml of acetonitrile. After heating under reflux for 20 hours, the cooled suspension was filtered, the filtrate was freed from solvent, the residue was taken up in ethyl acetate and the ethyl acetate mixture was washed with water, dried over sodium sulphate and freed from solvent. The residue from the ethyl acetate mixture crystallized out on adding isopropanol. After recrystallizing from ligroin/isopropanol, 154 g (60% of theory) of ω-(1,2,4-triazol-1-yl)-2,4-dichloroacetophenone of melting point 117° C. were obtained.

2nd stage

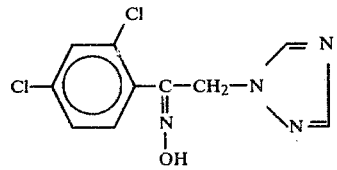

106.8 g (0.44 mol) of 1-(2,4-dichlorophenyl)-2-(1,2,4-triazol-1-yl)-ethan-1-one were dissolved in 780 ml of ethanol, 48 g of hydroxylammonium hydrochloride were added and the mixture was heated under reflux for 5 hours.

Thereafter, 1,000 ml of water were added to the reaction mixture and the mixture was filtered. 51 g (45% of theory) of ω-(1,2,4-triazol-1-yl)-2,4-dichloroacetophenone oxime of melting point 165°–170° C. were obtained.

Final stage

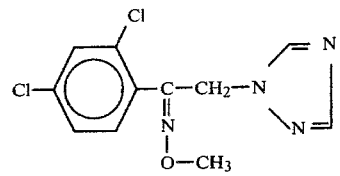

27.1 g (0.1 mol) of ω-(1,2,4-triazol-1-yl)-2,4-dichloroacetophenone oxime were suspended in 300 ml of toluene, 300 ml concentrated sodium hydroxide solution and 2 ml of benzyl-dimethyl-ammonium chloride, 28.4 g (0.2 mol) of methyl iodide were added and the mixture was stirred at 40° C. for 15 hours. It was then allowed to cool and the organic phase was separated off, washed three times with 200 ml of saturated sodium chloride solution each time, dried over sodium sulphate and concentrated by distilling off the solvent. The oil which remained also contained, in addition to the desired oxime ether, ω-(1,2,4-triazol-1-yl)-2,4-dichloroacetophenone, which was formed by saponification of the oxime employed. For purification, the oily residue was dissolved in 100 ml of chloroform, and 3 ml of concentrated nitric acid were added, while cooling with ice. After adding 100 ml of ether, 4.2 g of the nitrate of ω-(1,2,4-triazol-1-yl)-2,4-dichloroacetophenone oxime O-methyl ether were obtained as the pure stereoisomer of melting point 111° to 114° C. (decomposition). After distilling off the solvent in vacuo and recrystallizing the residue from ethyl acetate, a further 3.2 g of the nitrate of ω-(1,2,4-triazol-1-yl)-2,4-dichloroacetophenone oxime O-methyl ether were obtained as an isomer mixture of melting point 90°–92° C., whereupon a total of 7.4 g (17% of theory) of ω-(1,2,4-triazol-1-yl)-2,4-dichloroacetophenone oxime O-methyl ether were obtained. This corresponded to a total yield, over all the stages, of 4.6% of theory.

EXAMPLE B2

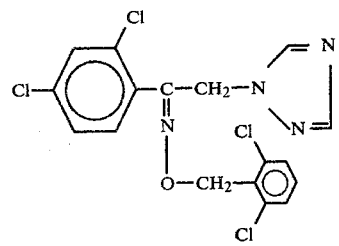

[Preparation according to the invention, but without isolation of the intermediate product]

8.9 g (0.04 mol) of ω-chloro-2,4-dichloroacetophenone were heated under reflux with 8.6 g (0.04 mol) of O-2,6-dichlorobenzyl-hydroxylamine hydrochloride and 3.3 g (0.04 mol) of sodium acetate in 100 ml of ethanol for 15 hours. 2.8 g (0.04 mol) of 1,2,4-triazole and 5.6 g (0.04 mol) of potassium carbonate were added to this reaction mixture and the mixture was heated under reflux for a further 20 hours. After cooling, it was filtered and the filtrate was concentrated. The residue was taken up in 250 ml of methylene chloride and the methylene chloride mixture was washed five times with 200 ml of water each time, dried over sodium sulphate and concentrated. 15.4 g (89.5% of theory) of ω-(1,2,4-triazol-1-yl)-2,4-dichloroacetophenone oxime O-2,6-dichlorobenzyl ether were obtained as an oil. For salt formation, this oil was dissolved in acetone. A solution of 5.4 g of 1,5-naphthalene-disulphonic acid in 25 ml of acetone was filtered in, the mixture was stirred at room temperature for 10 minutes and the precipitate was filtered off under suction. 14.8 g (72% of theory, relative to the base employed) of ω-(1,2,4-triazol-1-yl)-2,4-dichloroacetophenone oxime 2,6-dichlorobenzyl ether-1,5-naphthalenedisulphonate of melting point 245°–252° C. (decomposition) were obtained.

The following end products of the general formula

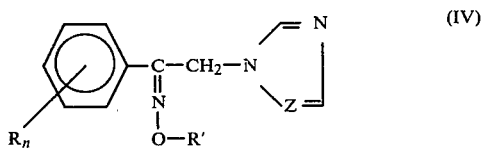

were obtained in a corresponding manner:

| Example No. | $R_n$ | R' | Z | Melting point (°C.) |
|---|---|---|---|---|
| B 3 | 2,4-Cl₂ | —CH₂—⌬—Cl | N | 130–35 (decomp.) (xHNO₃) |
| B 4 | 2,4-Cl₂ | —CH₂—⌬(Cl)—Cl | N | 135–137 (decomp.) (xHNO₃) |
| B 5 | 2,4-Cl₂ | C₂H₅ | N | 65–72 |
| B 6 | 2,4-Cl₂ | C₃H₇ | N | 108–12 |
| B 7 | 4-O—⌬—Cl | C₃H₇ | N | 154–56 (xHNO₃) |
| B 8 | 4-O—⌬—Cl | C₄H₉ | N | 53–55 |
| B 9 | 4-O—⌬—Cl | —CH₂—⌬(Cl)—Cl | N | 110–18 |
| B 10 | 4—⌬ | —CH₂—⌬(Cl)—Cl | N | 129–30 |
| B 11 | 4—⌬ | C₄H₉ | N | 129–30 |
| B 12 | 4—⌬—Cl | —CH₂—⌬(Cl)—Cl | N | 166 |
| B 13 | 4-O—⌬ | C₄H₉ | N | 142–44 (xHNO₃) |
| B 14 | 2,5-Cl₂ | —CH₂—⌬—Cl | N | 158–60 (xHCl) |
| B 15 | 3,4-Cl₂ | —CH₂—⌬(Cl)—Cl | N | 120–21 |
| B 16 | 2,4-Cl₂ | —CH₂—CH=CH₂ | N | 115 (decomp.) (xHNO₃) |
| B 17 | 2,4-Cl₂ | —CH₂—CH≡CH | N | 108 |
| B 18 | 4-Br | CH₃ | N | 157–59 (decomp.) (xHNO₃) (xHCl) |
| B 19 | 4-Br | —CH₂—⌬—Cl | N | 167–69 (xHCl) |
| B 20 | 4-Br | —CH₂—⌬(Cl)—Cl | N | 168–70 (xHCl) |
| B 21 | 4-Cl | CH₃ | N | 156–58 (xHCl) |
| B 22 | 4-Cl | —CH₂—⌬(Cl)—Cl | N | 91 |
| B 23 | 4-Cl | —CH₂—⌬(Cl)—Cl | CH | 127(xHCl) |
| B 24 | 2,4-Cl₂ | —CH₂—⌬(Cl)—Cl | CH | 137–38 (xHNO₃) |
| B 25 | 2,4-Cl₂ | —CH₂—⌬ | CH | 119–22 (xHNO₃) |
| B 26 | 2,4-Cl₂ | —CH₂—⌬—Cl | CH | 121–26 (xHNO₃) |
| B 27 | 4-Cl | —CH₂—⌬(Cl)—Cl | CH | 142–47 (xHNO₃) |
| B 28 | 2,4-(CH₃)₂ | —CH₂—⌬(Cl)—Cl | CH | 151–54 (xHNO₃) |
| B 29 | 4-Br | —CH₂—⌬(Cl)—Cl | CH | 152–54 (xHNO₃) |
| B 30 | 4-F | —CH₂—⌬(Cl)—Cl | CH | 124–26 (xHNO₃) |
| B 31 | 4—⌬ | —CH₂—⌬(Cl)—Cl | CH | 171–77 (xHNO₃) |
| B 32 | 4-O—⌬ | —CH₂—⌬ | CH | 93–100 (xHNO₃) |
| B 33 | 4-Cl | —CH₂—⌬(Cl)—Cl | CH | 152–55 (xHNO₃) |
| B 34 | 4-Cl | —CH₂—⌬(Cl) | CH | 116–18 (xHNO₃) |
| B 35 | 4-Cl | —CH₂—⌬(CH₃) | CH | 167–69 (xHNO₃) |
| B 36 | 4-Cl | —CH₂—⌬(Cl)—Cl | CH | 180(xHNO₃) |
| B 37 | 4-Cl | —CH₂—⌬(Cl)—F | CH | 170(xHNO₃) |

-continued

| Example No. | $R_n$ | R' | Z | Melting point (°C.) |
|---|---|---|---|---|
| B 38 | 4-Cl | —CH₂—⌬—Br | CH | 146(xHNO₃) |
| B 39 | 4-Br | —CH₂—⌬—Br | CH | 167(xHNO₃) |
| B 40 | 2,4-Cl₂ | —CH₂—⌬—Br | CH | 162–63 (xHNO₃) |
| B 41 | 4-Br | —CH₂—⌬—Cl | CH | 169–70 (xHNO₃) |
| B 42 | 4-Br | —CH₂—⌬(Cl)—Cl | CH | 163–64 (xHNO₃) |
| B 43 | 4-Cl | —CH₂—⌬—Cl | CH | 157–58 (xHNO₃) |
| B 44 | 4-Cl | C₂H₅ | CH | 117–119 |

It will be appreciated that the instant specification and examples are set forth by way of illustration and not limitation, and that various modifications and changes may be made without departing from the spirit and scope of the present invention.

What is claimed is:

1. An ω-halogeno-acetophenone oxime ether of the formula

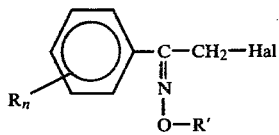

in which
R is fluorine, chlorine, bromine, nitro, cyano, alkyl or alkylsulphonyl with 1 to 4 carbon atoms, alkoxy or alkylthio with 1 to 2 carbon atoms, halogenoalkyl with up to 4 carbon atoms and up to 5 halogen atoms,
R' is alkyl, alkenyl or alkynyl with up to 4 carbon atoms, cycloalkylalkyl with 5 to 7 carbon atoms in the cycloalkyl moiety and 1 to 2 carbon atoms in the alkyl moiety, the cycloalkyl moiety being optionally substituted by alkyl with 1 to 4 carbon atoms, benzyl, styryl, or benzyl or styryl substituted by halogen, cyano, nitro, amino, alkyl with 1 to 4 carbon atoms, phenyl, phenoxy and/or halogenoalkyl with up to 2 carbon atoms and up to 3 identical or different halogen atoms,
n is 1, 2 or 3, and
Hal is halogen.

2. A compound according to claim 1, in which n is 1 to 2, and Hal is chlorine or bromine.

3. A compound according to claim 1, in which said compound is ω-chloro-2,4-dichloroacetophenone oxime O-2,6-dichlorobenzyl ether of the formula

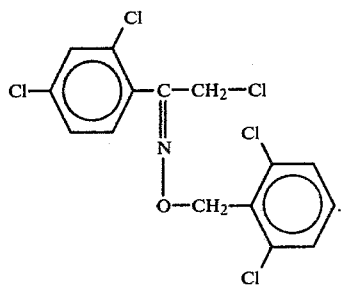

4. A compound according to claim 1, in which said compound ω-chloro-2,4-dichloroacetophenone oxime O-4-chlorobenzyl ether

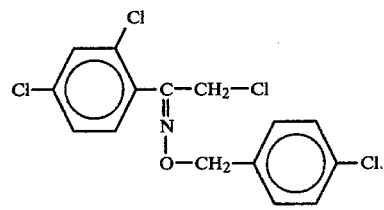

5. A compound according to claim 1, in which said compound is ω-chloro-4-p-chlorophenoxyacetophenone oxime O-2,4-dichlorobenzyl ether

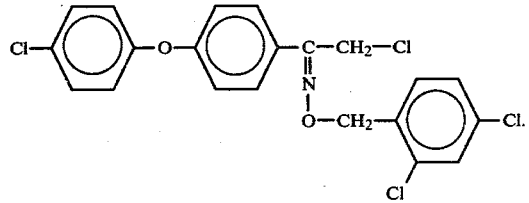

6. A compound according to claim 1, in which said compound is ω-chloro-2,4-dimethylacetophenone oxime O-2,4-dichlorobenzyl ether

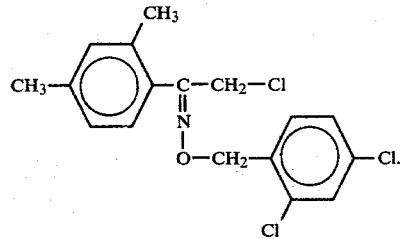

* * * * *

UNITED STATES PATENT AND TRADEMARK OFFICE
CERTIFICATE OF CORRECTION

PATENT NO. : 4,293,715

DATED : October 6, 1981

INVENTOR(S) : Wolfgang Kramer

It is certified that error appears in the above-identified patent and that said Letters Patent is hereby corrected as shown below:

Col. 15, line 25    Delete "were" and insert  --can be--

Signed and Sealed this

First Day of January 1985

[SEAL]

Attest:

Attesting Officer

GERALD J. MOSSINGHOFF

Commissioner of Patents and Trademarks